United States Patent [19]

Rosebrock et al.

[11] Patent Number: 4,857,103
[45] Date of Patent: Aug. 15, 1989

[54] INFLUENCING THE DEVELOPMENT OF CROPS WITH 7-CHLOROQUINOLINE-8-CARBOXYLIC ACIDS

[75] Inventors: Henning Rosebrock, Bad Durkheim; Johann Jung; Wilhelm Rademacher, both of Limburgerhof; Max Luib, Durkheim; Volker Fischer, Erpolzheim; Helmut Hagen, Frankenthal; Rolf-Dieter Kohler, Edingen-Neckarhausen; Juergen Markert, Mutterstadt, all of Fed. Rep. of Germany; Akihide Watanabe, Ayasei, Japan

[73] Assignee: BASF Aktiengesellschaft, Ludwigshafen, Fed. Rep. of Germany

[21] Appl. No.: 123,914

[22] Filed: Nov. 23, 1987

[30] Foreign Application Priority Data

Nov. 21, 1986 [DE] Fed. Rep. of Germany ....... 3639837

[51] Int. Cl.$^4$ ............................................. A01N 43/42
[52] U.S. Cl. ............................................. 71/94; 71/77
[58] Field of Search ....................... 71/94, 77; 514/311

[56] References Cited

U.S. PATENT DOCUMENTS

| 4,341,549 | 7/1982 | Large et al. | 71/86 |
| 4,497,651 | 2/1985 | Hagen et al. | 71/94 |
| 4,715,889 | 12/1987 | Hagen et al. | 71/94 |

FOREIGN PATENT DOCUMENTS

| 0541525 | 5/1957 | Canada | 514/311 |
| 104389 | 5/1962 | European Pat. Off. | 71/94 |
| 60429 | 3/1977 | European Pat. Off. | 71/94 |
| 0132752 | 11/1978 | Fed. Rep. of Germany | 71/94 |
| 0001149 | 1/1973 | Japan | 71/94 |
| 0650595 | 3/1979 | U.S.S.R. | 71/77 |

Primary Examiner—Glennon H. Hollrah
Attorney, Agent, or Firm—Keil & Weinkauf

[57] ABSTRACT

The development of crops is influenced by means of one or more 7-chloroquinoline-8-carboxylic acids of the general formula

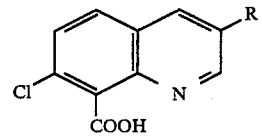

where R is fluorine, chlorine, bromine, $C_1$–$C_4$-alkyl, $C_1$–$C_4$-haloalkyl.

7 Claims, No Drawings

INFLUENCING THE DEVELOPMENT OF CROPS WITH 7-CHLOROQUINOLINE-8-CARBOXYLIC ACIDS

The present invention related to a method for influencing the development of crops.

7-chloroquinoline-8-carboxylic acids are disclosed in EP-A- 60,429 and EP-A- 104,389 and recommended there as herbicides.

We have found that 7-chloroquinoline-8-carboxylic acids

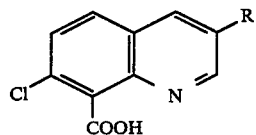

where R is fluorine, chlorine, bromine, $C_1$-$C_4$-alkyl, $C_1$-$C_4$-alkoxy or $C_1$-$C_4$-haloalkyl, are suitable for influencing the development of crops. When used in small amounts (sublethal range), they are capable of producing bioregulatory effects, for example an increase in yield, in crops.

R in formula I has the following specific meanings:
fluorine, chlorine or bromine, preferably fluorine or chlorine, particularly preferably chlorine,
straight-chain or branched $C_1$-$C_4$-alkyl, such as methyl, ethyl, n-propyl, isopropyl, n-butyl, isobutyl, sec-butyl or tert-butyl, preferably $C_1$-$C_3$-alkyl, such as methyl, ethyl or n-propyl, particularly preferably methyl or ethyl,
straight-chain or branched $C_1$-$C_4$-alkoxy, such as methoxy, ethoxy, n-propoxy, isopropoxy, n-butoxy, isobutoxy, sec-butoxy or tert-butoxy, preferably methoxy or ethoxy, and
straight-chain or branched $C_1$-$C_4$-haloalkyl, preferably $C_1$- or $C_2$-fluoro-, chloro- or bromoalkyl, particularly preferably methyl which is monosubstituted, disubstituted or trisubstituted by fluorine, chlorine or bromine, such as fluoromethyl, difluoromethyl, trifluoromethyl, chloromethyl, dichloromethyl, trichloromethyl, bromomethyl, dibromomethyl, tribromomethyl, chlorofluoromethyl, dichlorofluoromethyl, chlorodifluoromethyl, bromofluoromethyl, dibromofluoromethyl, bromodifluoromethyl, bromochloromethyl, chlorodibromomethyl, bromodichloromethyl or bromochlorofluoromethyl.

In particular, bioregulatory actions are obtained with 7-chloroquinoline-8-carboxylic acids of the formula I where R is chlorine, methyl or ethyl.

The 7-chloroquinoline-8-carboxylic acids of the formula I can be prepared by the processes described in EP-A-60,429 and EP-A-104,389.

The 7-chloroquinoline-8-carboxylic acids of the formula I can, when used in a small amount, have a bioregulatory effect on virtually all development stages of a plant, without having a harmful effect in terms of the intended success.

The wide variety of actions of the bioregulators depends in particular
(a) on the plant species and variety,
(b) on the time of application, based on the stage of development of the plant and on the season,
(c) on the place and method of application (seed dressing, tuber treatment, root or leaf application, treatment of individual flowers or inflorescences, etc.),
(d) on the geoclimatic factors, e.g. light intensity, length of day, temperature and amount of precipitation,
(e) on the nature of the soil (including fertiliser application),
(f) on the formulation and application form of the active ingredient and
(g) on the concentrations in which the active substance is used.

Of the number of different possible uses of the 7-chloroquinoline-8-carboxylic acids, a few are mentioned below:

A. The agents can be used to achieve higher yields, both of parts of plants and of plant ingredients. For example, it is possible to induce the growth of larger amounts of buds, flowers, leaves, fruit, seeds, roots and tubers.

Particularly in the case of vegetables and fruit, larger and more valuable fruit are obtained.

B. The 7-chloroquinoline-8-carboxylic acids can also be used to safeguard and accelerate the formation of fruit, even in seasons with an unfavorable climate.

C. The 7-chloroquinoline-8-carboxylic acids can be used to induce the formation of parthenocarpic fruit.

A particularly preferred use is for increasing the yield, for example in Solanaceae, such as aubergines, tomatoes, potatoes and paprika, Rosaceae, such as peaches, almonds, apples, pears and strawberries, in Fabaceae, such as soybean, peas and various species of beans, and Malvaceae, such as cotton and okra.

The active ingredients to be used according to the invention can be fed to the plants by seed dressing or via the soil, i.e. through the roots. Spraying the leaves or selectively spraying or immersing young infructescences is particularly preferred.

In seed treatment, from 0.0001 to 10 g, preferably from 0.0001 to 1 g, particularly preferably from 0.001 to 0.1 g, of active ingredient are generally required per kilogram of seed.

In dip treatments (for example for rooting seedlings, for application to seed potatoes or to eye cuttings of potatoes or for the selective treatment of individual flowers or inflorescences), concentrations of from 0.01 to 500, preferably from 0.1 to 100, particularly preferably from 0.1 to 80, ppm of active ingredient have proven suitable.

For the treatment of leaves and of the soil doses of not more than from 0.001 to 500, preferably from 0.01 to 100, particularly preferably from 0.1 to 50, g/ha are generally required.

The compounds I can be used in the form of conventional formulations, such as solutions, emulsions, suspensions, dusts, powders, pastes and granules. The forms for use depend entirely on the purposes; they should in any case ensure a fine and uniform distribution of the active substance. The formulations are prepared in a known manner, for example by diluting the active ingredient with solvents and/or carriers, if necessary with the use of emulsifiers and dispersants; where water is used as a diluent, other organic solvents may also be added. Suitable formulation assistants are essentially solvents, such as aromatics (e.g. xylene, toluene or benzene), chlorinated aromatics (e.g. chlorobenzenes), paraffins (e.g. mineral oil fractions), alcohols (e.g. methanol or butanol), amines (e.g. ethanolamine), N,N-dimethylformamide and water; solid carriers, such as ground natural minerals (e.g. kaolins, clays, talc or chalk) and ground synthetic minerals (e.g. finely divided silica or silicates); emulsifiers or other surfactants, such as non-ionic and anionic emulsifiers (e.g. polyoxyethylene fatty alcohol ethers or alkylsulfonates) and dispersants, such as lignin sulfite waste liquors and methylcellulose. The novel compounds are preferably used in aqueous solution, with or without the addition of water-miscible organic solvents, such as methanol or other lower alcohols, acetone, N,N-dimethylformamide or N-methylpyrrolidine. The formulations contain from 0.01 to 95, preferably from 0.05 to 90, particularly preferably from 0.05 to 20, % by weight of active ingredient.

The formulations or the ready-to-use preparations produced from them, e.g. solutions, emulsions, suspensions, powders, dusts, pastes or granules, are used in a conventional manner, for example by the preemergence method or postemergence method or as dressings.

Examples of formulations are:

2. parts by weight of compound 1 are well mixed with 3 parts by weight of the sodium salt of diisobutyl-naphthalene-alpha-sufonic acid, 17 parts by weight of the sodium salt of a lignin-sulfonic acid obtained from a sulfite waste liquor, and 78 parts by weight of powdered silica gel, and triturated in a hammer mill. By uniformly distributing the mixture in 20,000 parts by weight of water, a spray liquor is obtained containing 0.01% by weight of the active ingredient.

II. 3 parts by weight of compound 1 are intimately mixed with 97 parts by weight of particulate kaolin. A dust is obtained containing 3% by weight of the active ingredient.

III. 3 parts by weight of compound 2 are intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 4 parts by weight of compound 1 are intimately mixed with 20 parts of the sodium salt of a phenol-sulfonic acid-urea-formaldehyde condensate, 4 parts of silica gel and 72 parts of water to give a stable aqueous dispersion. Dilution in 100,000 parts by weight of water gives an aqueous dispersion containing 0.004% by weight of active ingredient.

V. 2 parts of compound 3 are intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 86 parts of a paraffinic mineral oil. A stable oily dispersion is obtained.

VI. 90 parts by weight of compound 2 are mixed with 10 parts by weight of N-methyl-alpha-pyrrolidone. A solution is obtained which is suitable for application in the form of very fine drops.

VII. 0.2 part by weight of compound 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.0002% by weight of the active ingredient.

VIII. 0.1 part by weight of compound 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.0001% by weight (1 ppm) of the active ingredient.

IX. 0.1 part by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 10,000 parts by weight of water and uniformly distributing it therein, an aqueous dispersion is obtained containing 0.001% by weight of the active ingredient.

The 7-chloroquinoline-8-carboxylic acids and the agents containing them can be used together with other active ingredients, for example with insecticides, other bioregulators and fungicides, or may be mixed with fertilizers. When they are mixed with bioregulators, synergistic effects also occur, i.e. the activity of the combination may be greater than that of the individual components in corresponding amounts. Examples of use The following specific compounds were investigated:

Compound no. 1: 3,7-dichloroquinoline-8-carboxylic acid

Compound no. 2: 7-chloro-3-methylquinoline-8-carboxylic acid and

Compound no. 3: 7-chloro-3-ethylquinoline-8-carboxylic acid.

The following known bioregulators were used for comparison:

A: 4-(2-methyl-4-chlorophenoxy)-butyric acid (MCPB, contained in the commercial product MADEC);

B: Gibberellin A$_3$ (GA3);

C: 4-chlorophenoxyacetic acid (4-CPA, contained in the commercial product TOMATOTONE).

EXAMPLE 1

Quantitative and qualitative improvement of fruit development in aubergines (single use)

Aubergines of the Kurokoma variety were grown under greenhouse conditions in plastic pots (30.5×27.0 cm). The substrate used was standard soil. All plants in a trial were uniformly watered and supplied with fertilizer, as required.

At the beginning of flowering, the plants were sprayed once with a formulation, until dripping wet; the amounts used, which are stated in Table 1 below in ppm, denote the concentration of the agent in an aqueous solution. 1 ppm corresponds to an amount of 0.8 g of active ingredient per hectare.

After 50 days, the trial was evaluated. It was found that compound no. 1 reduces the number of fruit but at the same time the overall fruit yield and in particular the proportion of useful fruit having a length of more than 12 cm and an individual weight of not less than 50 g were substantially improved.

Concentrations above 250 ppm brought no further improvement. (The yield stated is a mean value and is based on 5 plants in each case).

TABLE 1

| Compound no. | Concentration of the spray liquor (ppm) | Number of fruit | | Fruit weight (g) | |
|---|---|---|---|---|---|
| | | Total | More than 50 g/fruit | Total | More than 50 g/fruit |
| Control | 0 | 58 | 0 | 250 | 0 |
| 1 | 10 | 16 | 14 | 1052 | 1018 |
| 1 | 50 | 19 | 15 | 1243 | 1229 |
| 1 | 250 | 18 | 10 | 834 | 681 |
| 1 | 750 | 17 | 7 | 844 | 679 |
| B | 50 | 42 | 4 | 462 | 309 |

EXAMPLE 2

Quantitative and qualitative improvement of fruit development in aubergines (double application)

Aubergines of the Kurokoma variety were cultivated as described in Example 1.

At the beginning of flowering and 66 days later, the plants were sprayed to runoff with a solution of active ingredient (1 ppm denotes 0.8 g of active ingredient per hectare). 85 days after flowering, the trial was evaluated. It was found that, by using compound no. 1, the proportion of marketable fruit having a length of more than 12 cm and an individual weight of more than 50 g could be substantially increased. The following specific results were achieved here (yields in each case averaged and based on 5 plants):

TABLE 2

| Compound no. | Concentration of the spray liquor (ppm) | Number of fruit | | Fruit weight (g) | |
|---|---|---|---|---|---|
| | | Total | More than 50 g/fruit | Total | More than 50 g/fruit |
| Control | 0 | 141 | 24 | 2073 | 1196 |
| 1 | 5 | 116 | 19 | 1831 | 1179 |
| 1 | 10 | 112 | 30 | 2040 | 1484 |
| 1 | 20 | 102 | 38 | 2501 | 2152 |
| 1 | 40 | 100 | 36 | 2393 | 2146 |
| A | 40 | 118 | 26 | 2104 | 1563 |

EXAMPLE 3

Quantitative and qualitative improvement of fruit development in aubergines (triple application)

Aubergines of the Senryo variety were cultivated as described in Example 1. The plants were sprayed three times, in each case to runoff wet (1 ppm denotes 1.25 g of active ingredient per hectare).

Date 1: 20 days after transplanting the seedlings
Date 2: 30 days after transplanting the seedlings
Date 3: 40 days after transplanting the seedlings.

42 days after the first treatment, the trial was evaluated. It was found that the use of compounds no. 1 and no. 2 (5 ppm and 10 ppm, and 5 ppm, respectively) led to a substantially higher yield. In particular, the proportion of fruit with an individual weight of more than 50 g was higher than in the case of the comparison. The numbers stated in Table 3 are based on the yield of 6 plants in each case:

TABLE 3

| Compound no. | Concentration of the spray liquor (ppm) | Number of fruit | | Fruit weight (g) | |
|---|---|---|---|---|---|
| | | Total | More than 50 g/fruit | Total | More than 50 g/fruit |
| Control | 0 | 32 | 9 | 971 | 550 |
| 1 | 5 | 21 | 14 | 1380 | 1109 |
| 1 | 10 | 27 | 13 | 1315 | 1013 |
| 1 | 20 | 20 | 13 | 1004 | 889 |
| 1 | 40 | 23 | 15 | 1214 | 1116 |
| 2 | 5 | 22 | 13 | 1230 | 957 |
| 2 | 20 | 32 | 14 | 1266 | 911 |
| 2 | 40 | 29 | 16 | 1361 | 1034 |
| A | 40 | 16 | 8 | 789 | 636 |

EXAMPLE 4

Quantitative and qualitative improvement of fruit development in tomatoes (treatment of the entire shoot)

Tomatoes of the Homare 114 variety were grown under greenhouse conditions in plastic pots (30.5×27.0 cm). The substrate used was standard soil. All plants in a trial were uniformly watered and supplied with fertilizer, as required. In accordance with general practice, side shoots were regularly removed. At the time of flowering of the first infructescence, the plants were sprayed to runoff with a solution of active ingredient. 1 ppm corresponds in each case to an amount of 1 g/ha. 75 days later, the trial was evaluated. In this trial, it was found that treatment with compound 1 substantially reduced the number of fruit, particularly on the younger inflorescences. However, the remaining fruit had a substantially higher individual weight and total weight than the untreated fruit, so that the market-ability may be expected to be improved. The numerical values shown in Table 4 are based in each case on 5 plants.

TABLE 4

| Compound no. | Concentration of the spray liquor (ppm) | Number of fruit (Pieces) | Fruit yield (g) | Mean fruit weight (g) |
|---|---|---|---|---|
| Control | 0 | 107 | 3797 | 35.5 |
| 1 | 1 | 88 | 4318 | 49.1 |
| 1 | 5 | 39 | 4605 | 118.1 |
| 1 | 10 | 39 | 4915 | 126.0 |

EXAMPLE 5

Quantitative and qualitative improvement of fruit development in tomatoes (treatment of the infructescences)

he plants were grown as described in Example 4. At the time of flowering of the first infructescence, all infructescences were to runoff sprayed with solutions of active ingredient (1 ppm corresponds to 0.1 g of active ingredient per ha). 75 days later, the trial was evaluated.

In contrast to the treatment of the entire plant (Example 4), treatment with compound no. 1 resulted in a reduction of the number of fruit by only about 25-30%. The total fruit yield was once again substantially increased, the major part being accounted for by the oldest infructescence. Moreover, the treatment resulted in a higher weight of individual fruit.

The yields stated in Table 5 are based in each case on 5 plants.

TABLE 5

| Compound no. | Concentration of the spray liquor (ppm) | Number of fruit (Pieces) | Fruit yield (g) | Mean fruit weight (g) |
| --- | --- | --- | --- | --- |
| Control | — | 107 | 3797 | 35.5 |
| 1 | 10 | 82 | 4514 | 55.0 |
| 1 | 20 | 72 | 4571 | 63.5 |
| C | 20 | 97 | 3970 | 40.9 |

EXAMPLE 6

Improvement of fruit quality for tomatoes

Tomatoes of the Curabel variety were cultivated in the usual season, under field conditions. Cultivation of the plants was carried out under conditions corresponding to practice. At the time of flowering of a raceme, the plants were sprayed with an aqueous formulation of the novel compounds (a total of five successive treatments).

The novel substances resulted in an increased yield, similarly to Examples 4 and 5. Additional investigations showed that the novel compounds lead to fruit growth without seed formation (parthenocarpy) (Table 6). Furthermore, it was found that, under the influence of, for example, compounds 1 and 2, firmer fruit pulp is obtained. The stated effects are thus expected to lead to an improvement in quality both in vegetable tomatoes and in industrial tomatoes.

TABLE 6*

| Compound no. | Application rate (g of active ingredient/ha) | Average number of seeds per fruit |
| --- | --- | --- |
| Control | 0 | 109 |
| 1 | 0.315 | 110 |
| 1 | 0.625 | 58 |
| 1 | 1.250 | 35 |
| 1 | 2.500 | 19 |
| 1 | 5.000 | 5 |
| 2 | 5.000 | 70 |
| C | 12.500 | 80 |

*20 fruit of uniform size and weighing about 80 g each were used per trial treatment.

EXAMPLE 7

Acceleration of fruit development in aubergines

Aubergines of the Kurokoma variety were cultivated as stated in Example 1. The trial was carried out during fall and winter, i.e. during seasons in which it is considered difficult to produce aubergine fruit. The plants were shown on the September 27th and the treatment carried out on December 25th by spraying to runoff (1 ppm corresponds to 0.6 g of active ingredient per hectare).

It was found that treatment of the plants with compound 1 resulted in a reduction in the number of flowers per plant, but fruit development was substantially accelerated.

TABLE 7

| Compound no. | Concentration of the spray Liquor (ppm) | Fruit yield per plant (g) | | | |
| --- | --- | --- | --- | --- | --- |
| | | on 24.01 | on 04.02 | on 10.02 | Total |
| Control | 0 | 0 | 0 | 0 | 0 |
| 1 | 10 | 94.2 | 81.7 | 27.6 | 203.5 |
| 1 | 50 | 124.0 | 66.0 | 43.7 | 233.7 |
| 1 | 250 | 97.5 | 8.8 | 29.8 | 136.1 |
| 1 | 750 | 93.2 | 33.1 | 9.4 | 135.7 |
| B | 50 | 15.8 | 45.9 | 0 | 61.7 |

EXAMPLE 8

Increase in yield of cotton

Cotton of the Delta Pine variety was cultivated in the open in Greenville, Miss., USA. During the main flowering period, flowers and buds were selectively sprayed with a solution of active ingredient.

It was found that compound 1 resulted in a substantial increase in yield. The following specific results were obtained:

TABLE 8

| Compound no. | Application rate (g of active ingredient/ha) | Yield (kg/ha) |
| --- | --- | --- |
| Control | 0 | 2725 |
| 1 | 10 | 3018 |
| 1 | 30 | 3588 |
| 1 | 60 | 2997 |
| 1 | 80 | 3074 |

EXAMPLE 9

Quantitative and qualitative improvement of tuber development in potatoes

Eye cuttings of potatoes (Kennebec variety) were first placed in an aqueous solution of the novel active ingredients for about 10 minutes and then planted out. The potato plants were cultivated under conventional conditions.

It was found that a treatment with, for example, compound 2 resulted in a substantial increase in both the total yield of potato tubers and the proportion of marketable tubers (tubers having a diameter of more than 8 cm).

The associated yield data are stated in Table 9 and are based on a plot size of 13 m$^2$.

TABLE 9

| Compound no. | Concentration of the treatment solution (ppm) | Number of potato tubers | | Tuber yield (kg) | |
| --- | --- | --- | --- | --- | --- |
| | | Total | Marketable | Total | Marketable |
| Control | 0 | 339 | 86 | 16.5 | 10.3 |
| 2 | 1 | 378 | 110 | 19.5 | 12.8 |
| 2 | 10 | 361 | 112 | 18.7 | 12.4 |

EXAMPLE 10

Improvement of the fruit yield in peaches 3 year old peach trees (Red Haven and Elberta Queen varieties) were sprayed to runoff with an aqueous formulation of the novel substances at the time of flowering (750 ml/tree). The plants were cultivated under conventional conditions and the fruit was harvested at the usual time.

As shown in Tables 10a and 10b, treatment with the active ingredients resulted in an increase in the fruit yield. Furthermore, in the case of the Red Haven variety, setting of the fruit was improved and ripening of the fruit accelerated, which is desirable in many cases. In the Elberta Queen variety, compound 2 led to an increase of about 10% in the fruit size, so that improvement marketability may be expected.

The data given are mean values and are based in each case on one tree.

TABLE 10a

| Compound no. | Concentration of the spray solution (ppm) | Red Haven variety Harvested fruit | | | | Total yield (kg) |
|---|---|---|---|---|---|---|
| | | Number | % unripe | % ripe | Mean fruit weight (g) | |
| Control | 0 | 148.7 | 60 | 40 | 85 | 12.64 |
| 1 | 5 | 154.0 | 55 | 45 | 87 | 13.40 |
| 1 | 10 | 190.0 | 41 | 59 | 70 | 13.30 |
| 2 | 20 | 183.4 | 27 | 73 | 83 | 15.22 |

TABLE 10b

| Compound no. | Concentration of the spray solution (ppm) | Elberta-Queen variety Harvested fruit | | | | Total yield (kg) |
|---|---|---|---|---|---|---|
| | | Number | % unripe | % ripe | Mean fruit weight (g) | |
| Control | 0 | 47.0 | 23 | 77 | 125 | 5.88 |
| 1 | 5 | 69.0 | 28 | 72 | 124 | 8.56 |
| 1 | 20 | 53.3 | 26 | 74 | 125 | 6.66 |
| 2 | 10 | 43.7 | 15 | 85 | 136 | 5.94 |
| 2 | 20 | 47.0 | 28 | 72 | 140 | 6.58 |
| 2 | 40 | 57.0 | 25 | 75 | 138 | 7.83 |

EXAMPLE 11

Increase in yield of strawberries (dip-treatment of seedlings)

The root region of strawberry seedlings (Earliglow variety) was immersed in an aqueous formulation of the novel substances directly before transplanting. Further cultivation of the plants was carried out under field conditions conventionally employed in practice. With the onset of ripening, ripe fruit were harvested at intervals of 4 days. In conformity with the conventional practice, a total of four harvests were gathered. It would not have been profitable to harvest the fruit which still remained.

As shown in Table 11, such a treatment results in a higher overall yield, which is principally due to increased setting of the fruit. It is also advantageous that the fruit from treated plants were ripe for harvesting at an earlier stage.

The data are based in each case on 25 plants from a plot of 6.5 m².

EXAMPLE 12

Increase in yield of strawberries (leaf treatment)

One year old strawberry plants of the Earliglow variety (cultivated under conventional field conditions) were treated during the principal flowering period with an aqueous formulation of the novel compounds (375 1/ha). As shown in Table 12 the fruit yield (sum of all individual harvests) can be substantially increased by a treatment of this type. As in Example 11, in this case too the increase in yield is primarily due to improved setting of the fruit.

The data are based in each case on 10 plants.

TABLE 12

| Compound no. | Application rate (g of active ingredient/ha) | Total yield | |
|---|---|---|---|
| | | Number | Weight (g) |
| Control | 0 | 70.8 | 335.0 |
| 1 | 0.125 | 72.9 | 345.1 |
| 1 | 0.250 | 82.1 | 395.3 |
| 1 | 0.500 | 76.5 | 368.5 |
| 2 | 0.125 | 72.9 | 351.8 |
| 2 | 0.250 | 74.3 | 361.8 |

EXAMPLE 13

Increase in yield of soybean

Soybean plants of the Sertaneja and IAS 5 varieties were cultivated in the open under conditions conventionally used in practice. The plants were sprayed with an aqueous formulation of the novel substances at the onset of flowering. As shown in Table 13, the yield of seed can be substantially increased by a treatment of this type.

TABLE 11

| Compound no. | Concentration of the treatment solution (ppm) | 1st harvest | | 2nd harvest | | 3rd harvest | | 4th harvest | | Total yield | |
|---|---|---|---|---|---|---|---|---|---|---|---|
| | | Number of fruit | Weight (g) | Number of fruit | Weight (g) | Number of fruit | Weight (g) | Number of fruit | Weight (g) | Number of fruit | Weight (g) |
| Control | 0 | 15.0 | 116.0 | 77.0 | 482.0 | 57.5 | 167.0 | 39.0 | 104.0 | 188.5 | 869.0 |
| 2 | 1 | 18.5 | 169.4 | 96.3 | 583.2 | 72.5 | 205.4 | 41.7 | 99.8 | 229.0 | 1057.8 |
| 2 | 10 | 23.3 | 196.0 | 95.5 | 554.3 | 55.2 | 173.7 | 36.7 | 104.0 | 210.7 | 1027.7 |

TABLE 13

| Compound no. | Application rate (g of active ingredient/ha) | Seed yield (t/ha) Sertaneia | IAS 5 |
|---|---|---|---|
| Control | 0 | 3.07 | 1.68 |
| 1 | 1 | 3.32 | 1.78 |
| 1 | 5 | 3.22 | 1.81 |

EXAMPLE 14

Increase in yield of lima beans (leaf treatment)

Lima beans of the Jackson Wonder variety were cultivated under conventional field conditions, and sprayed with an aqueous formulation of the novel substances (350 l/ha) at the time of principal flowering.

As shown in Table 14, a treatment of this type results in substantially increased setting of beans and hence in an increase in the yield in terms of weight.

The data are based in each case on trial plots of 7.5 m².

TABLE 14

| Compound no. | Application rate (g of active ingredient/ha) | Number of fruit | Weight of fruit (kg) |
|---|---|---|---|
| Control | 0 | 1128 | 3.86 |
| 1 | 1.0 | 1282 | 4.31 |
| 2 | 1.0 | 1222 | 3.96 |
|  | 2.0 | 1365 | 4.44 |

EXAMPLE 15

Improvement in the fruit setting of lima beans (seed treatment)

Before being sown, seeds of lima beans (Jackson Wonder variety) were dressed with an aqueous formulation of the novel substances. The plants were cultivated in individual plots (6.5 m²) in conformity with conventional practice and under field conditions. The setting of the fruit and the ripeness of the beans were determined for 10 randomly removed plants at the usual harvest time. As shown in Table 15, the novel substances lead to a substantial increase in setting of the fruit, which is also likely to give a higher yield in terms of weight. The Table also shows that ripening of the fruit under the influence of the novel compounds begins at an earlier stage.

TABLE 15

| Compound no. | Application rate (g of active ingredient/100 kg) | Number of fruit Unripe | Ripe | Total |
|---|---|---|---|---|
| Control | 0 | 30 | 280 | 310 |
| 1 | 0.01 | 39 | 364 | 403 |
|  | 0.10 | 28 | 412 | 440 |
| 2 | 0.01 | 32 | 308 | 340 |
| 3 | 0.10 | 29 | 339 | 368 |
|  | 1.00 | 28 | 347 | 375 |
|  | 5.00 | 29 | 344 | 373 |

EXAMPLE 16

Acceleration of open-air emergence in cotton and corn

Seeds of cotton (Stoneville 825 variety) and corn (Funk's 4733 variety) were dressed with an aqueous formulation of the novel substances. The emergence was determined six and ten days after transplanting into the open. As shown in Table 16, the process of emergence of the seed is accelerated by the novel compounds. Better overall growth of the plants and hence an increased yield may therefore be expected.

TABLE 16

| Compound no. | Application rate (g of active ingredient/100 kg) | % Open-air emergence in cotton 6 days after transplanting | 10 days after transplanting | % Open-air in corn 6 days after transplanting | 10 days after transplanting |
|---|---|---|---|---|---|
| Control | 0 | 50 | 86 | 36 | 99 |
| 1 | 0.1 | 56 | 82 | 48 | 100 |
| 2 | 0.1 | 61 | 86 | 44 | 98 |
|  | 1.0 | 62 | 84 | 51 | 98 |

We claim:

1. A method of increasing the yield and/or quality of Solanaceae, Rosaceae, Fabaceae or Malavaceae which comprises: applying to the crops, to the soil in which the crops are planted or are to be planted or to the seeds of the crops a yield increasing and/or quality improving amount of 0.0001 to 10 g per kilogram of seed for seed treatment, 0.001 to less than 50 g per hectare for crop treatment and/or soil treatment or 0.001 to 100 ppm for seedling, tuber or inflorescence treatment of one or more 7-chloroquinoline-8-carboxylic acids of the formula I

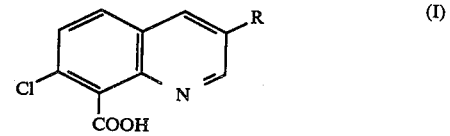

Where r is fluorine, chlorine, bromine, $C_1$-$C_4$-alkyl, $C_1$-$C_4$-alkoxy or $C_1$-$C_4$-haloalkyl.

2. A method as defined in claim 1, wherein, for seed treatment, from 0.0001 to 10 g of a 7-chloroquinoline-8-carboxylic acid I are used per kilogram of seed.

3. A method as defined in claim 1, wherein, for leaf treatment and/or soil treatment, from 0.001 to 100 g of a 7-chloroquinoline-8-carboxylic acid I are used per hectare.

4. A method as defined in claim 1, wherein, for the treatment of seedlings, tubers or inflorescences in a dip bath, from 0.01 to 100 ppm of a 7-chloroquinoline-8-carboxylic acid I are used.

5. A method as defined in claim 1, wherein the crops are Solanaceae.

6. A method as defined in claim 1, wherein the substituent R in a 7-chloroquinoline-8-carboxylic acid of the formula I is fluorine, chlorine, methyl, ethyl, n-propyl, methoxy, ethoxy or $C_1$- or $C_2$-fluoro-, chloro- or bromoalkyl.

7. A method as defined in claim 1, wherein the substituent R in a 7-chloroquinoline-8-carboxylic acid of the formula I is chlorine, methyl or ethyl.

* * * * *

UNITED STATES PATENT AND TRADEMARK OFFICE
CERTIFICATE OF CORRECTION

PATENT NO. : 4,857,103
DATED : August 15, 1989
INVENTOR(S) : Henning ROSEBROCK et al.

It is certified that error appears in the above—identified patent and that said Letters Patent is hereby corrected as shown below:

Column 12, claim 1, line 27, should read as follows:

-- treatment and/or soil treatment or 0.01 to 100ppm for --

Signed and Sealed this

Twelfth Day of June, 1990

Attest:

HARRY F. MANBECK, JR.

Attesting Officer      Commissioner of Patents and Trademarks